United States Patent [19]

Nakano et al.

[11] Patent Number: 5,380,878
[45] Date of Patent: Jan. 10, 1995

[54] BENZO[B]THIOPHEN-5-YL DERIVATIVE AND PROCESS FOR PRODUCING THE SAME

[75] Inventors: Joji Nakano, Toyama; Nobuhisa Taya, Shinminato; Hisaaki Chaki; Tetsuo Yamafuji, both of Toyama; Kaishu Momonoi, Shinminato, all of Japan

[73] Assignee: Toyama Chemical Co., Ltd., Tokyo, Japan

[21] Appl. No.: 217,960

[22] Filed: Mar. 29, 1994

Related U.S. Application Data

[63] Continuation of Ser. No. 42,510, Apr. 5, 1993, abandoned.

[30] Foreign Application Priority Data

Apr. 13, 1992 [JP] Japan .................................. 4-119740
Mar. 25, 1993 [JP] Japan .................................. 5-090934

[51] Int. Cl.$^6$ ................. C07D 333/52; C07D 307/78; C07D 333/56; C07D 333; C07D 58
[52] U.S. Cl. ........................................ 549/60; 549/57; 549/58; 549/440; 549/447
[58] Field of Search ....................... 549/60, 57, 58, 440, 549/447, 441

[56] References Cited

U.S. PATENT DOCUMENTS

| | | |
|---|---|---|
| 4,791,107 | 1/1988 | Hamer et al. |
| 4,810,722 | 3/1989 | Toja et al. |
| 4,829,079 | 5/1989 | Toja et al. |
| 4,839,364 | 6/1989 | Shutake et al. |
| 4,851,414 | 7/1989 | Shiozaki et al. |
| 4,859,666 | 8/1989 | Elson et al. |
| 4,877,790 | 10/1989 | Iemura et al. |
| 4,990,516 | 2/1991 | Ohashi et al. |

FOREIGN PATENT DOCUMENTS

| | | |
|---|---|---|
| 2009886 | 8/1990 | Canada . |
| 0383281 | 8/1990 | European Pat. Off. . |
| 8101408 | 5/1981 | WIPO . |

OTHER PUBLICATIONS

Chemical Abstracts, vol. 117, abstract No. 90114b, No. 9, 31 Aug. 1992, p. 765, col. L, Columbus, Ohio, US.
Derwent Publications Ltd., London, GB; 2 pages, AN 92-156267 & JP-A-4 095 070 (Toyoma Chem Co) *abstract* (1992).
"Protective Effect of R(−)—1-Benzo[b]thiophen-5-yl)2-[2-(N,N-diethylamino)ethoxy]ethanol Hydrochloride (T-588), a Novel Cerebral Activator, against Experimental Cerebral Anoxia"; Satoshi Ono, et al; *Japan. J. Pharmacol.* 62, 81–86 (1993).
"Oral Tetrahydroaminoacridine in Long-Term Treatment of Senile Dementia, Alzheimer Type"; William Koopmans Summers, M.D., et al; *The New England Journal of Medicine*; vol. 315, No. 20; Nov. 13, 1986.
"Randomized Placebo-controlled Double-blind Cross-over Study on Antihypoxidotic Effects of Piracetam Using Psychophysiological Measures in Healthy Volunteers"; K. Schaffler, et al; *Arzneim-Forsch/Drug Res*, 38(I), Nr. 2 (1988).
"Transient Hypoxic-Amnesia: Evidence For a Triphasic Memory-Consolidating Mechanism with parallel Processing"; Brina Frieder, et al; *Behavioral Biology* 22, pp. 178–179 (1978).
"Effects of Hypoxia on Memory Consolidation: Implications For a Multistage Model of Memory"; Cecil Allweis, et al; *Behavioral Brain research*, 11 (1984), pp. 117–121.
"Influence of Training Strength on Amnesia Induced by Pretraining Injections of Cycloheximide"; James F. Flood; *Physiology and Behavior*, vol. 9, pp. 589–600 (1972).
"Protein Synthesis Inhibition and Amnesia for Saccharin Aversion Memory in Rats After Intra-Cisternal Administration of Cycloheximide"; A. R. Tucker, et al; *Physiology & Behavior*, vol. 28, pp. 1025–1028 (1982).
"Isomerization-Crystallization Method in Optical Resolution"; Kazutaka Arai; *Journal of Organic Synthetic Chemical Society*, vol. 44, No. 6, pp. 486–498 (1986).

Primary Examiner—Allen J. Robinson
Assistant Examiner—Deborah Lambkin
Attorney, Agent, or Firm—Oblon, Spivak, McClelland, Maier & Neustadt (Abstract continued on next page.)

[57] ABSTRACT

This invention relates to a process for producing a compound represented by formula (6a) or (6b):

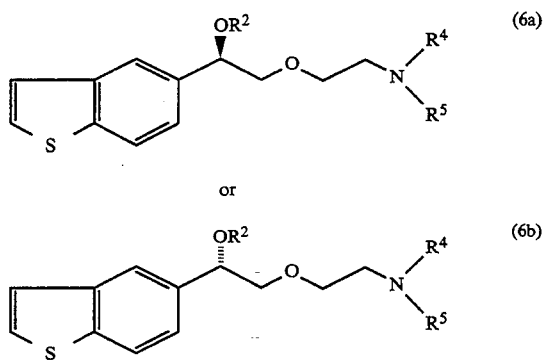

wherein $R^2$ represents a hydrogen atom or a hydroxyl-protecting group and $R^4$ and $R^5$, which may be the same or different, represents lower alkyl groups, using a compound represented by formula (2a) or (2b) obtained by preferential crystallization:

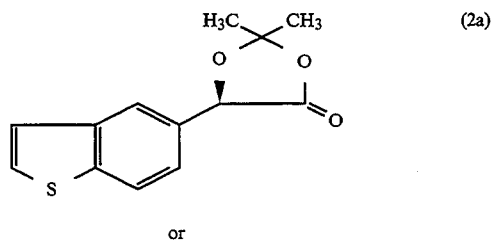

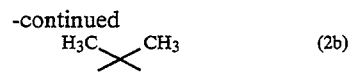

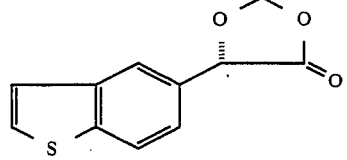

and also to a compound represented by the following formula (7) which is an intermediate useful for producing the compound of formula (6a) or (6b):

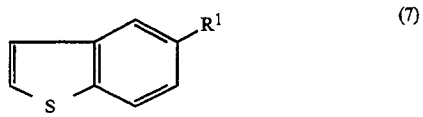

wherein $R^1$ represents a group represented by formula (8):

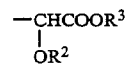

wherein $R^2$ and $R^3$ is as defined above and $R^3$ represents a hydrogen atom, a group or a carboxyl protecting group represented by formula (9):

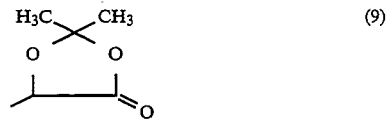

or a group represented by formula (10):

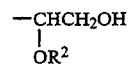

wherein $R^2$ is as defined above.

6 Claims, No Drawings

BENZO[B]THIOPHEN-5-YL DERIVATIVE AND PROCESS FOR PRODUCING THE SAME

This application is a continuation of application Ser. No. 08/042,510, filed on Apr. 5, 1993, now abandoned.

This invention relates to a process for producing a compound represented by formula (6) or a salt thereof which is useful as a cerebral function-improving agent:

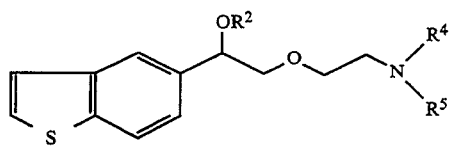

wherein $R^2$ represents a hydrogen atom or a hydroxyl-protecting group and $R^4$ and $R^5$ which may be the same or different, represent lower alkyl groups, and to an intermediate therefor.

A process for producing a compound of formula (6) or its salt which is useful as a cerebral function-improving agent is disclosed in Japanese Patent Application Kokai (Laid-Open) No. 4-95,070. When optical active compounds represented by formulas (6a) and (6b) and their salts are intended to be obtained:

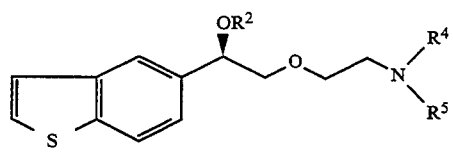

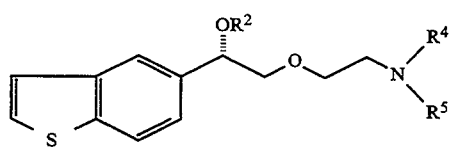

wherein $R^2$, $R^4$ and $R^5$ are as defined above, the conventional resolution method enables the optical active compounds to be produced from the compound of formula (6) in only a yield of about 30–40%. In addition, it requires use of an expensive optical resolution agent.

Under such circumstances, the present inventors have made extensive research on a process for producing a compound of formula (6) or its salt, in particular, its optically active compound, at a low price, in a high yield and on a commercial scale. As a result, they have found that a production process through a benzo[b]thiophen-5-yl derivative represented by formula (7), its optically active compound or a salt thereof:

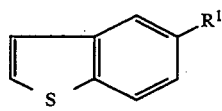

wherein $R^1$ represents a group represented by formula (8):

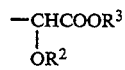

wherein $R^2$ is as defined above and $R^3$ represents a hydrogen atom or a carboxyl-protecting group, a group represented by formula (9):

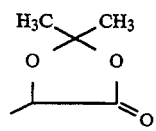

or a group represented by formula (10):

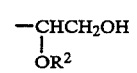

wherein $R^2$ is as defined above is very useful and that in particular, an optically active form of a compound of formula (7) in which $R^1$ is a 2,2-dimethyl-4-oxo-1,3-dioxolan-5-yl group can be produced inexpensively in a high yield on a commercial scale by a quite unexpected racemization-preferential crystallization method.

An object of this invention is to provide a novel process for producing an optically active compound represented by formula (6a) or (6b) or its salt.

Another object of this invention is to provide a novel process for producing in a high yield an optically active compound represented by formula (6a) or (6b) or its salt with high purity.

A further object of this invention is to provide a novel intermediate represented by formula (7).

Other objects and advantages of this invention will become apparent from the following description.

According to this invention, there is provided a process for producing an optically active benzo[b]thiophen-5-yl derivative represented by formula (6a) or (6b) or its salt:

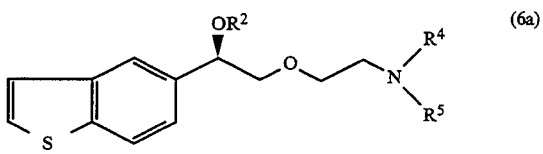

or

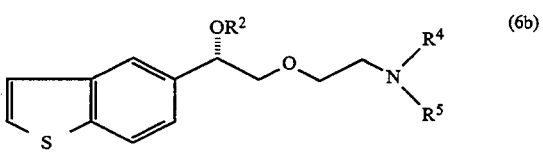

wherein $R^2$ $R^4$ and $R^5$ are as defined above, which comprises inoculating into a supersaturated solution of a compound represented by formula (1):

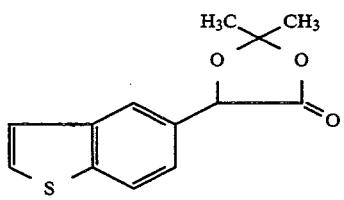

(1)

seed crystals of an optically active compound of formula (2a) when production of the compound of formula (6a) is intended or seed crystals of an optically active compound of formula (2b) when production of the compound of formula (6b) is intended, in the presence of a racemization catalyst to crystallize preferentially a corresponding optically active form of the compound of formula (1), to obtain, respectively, an optically active compound represented by formula (2a):

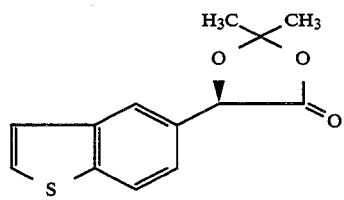

(2a)

or formula (2b):

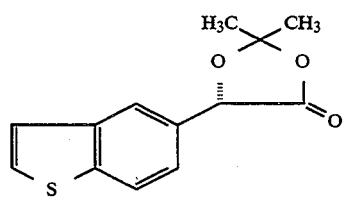

(2b)

then subjecting the optically active compound obtained to alcoholysis or hydrolysis in the presence of an acid catalyst, subsequently introducing into the resulting product a hydroxyl-protecting group in a manner known per se to obtain, respectively, an optically active compound represented by formula (3a):

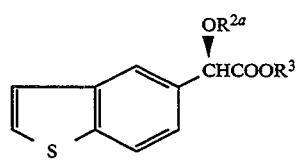

(3a)

or formula (3b):

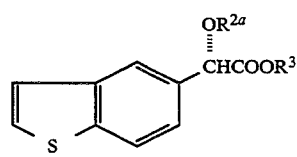

(3b)

wherein $R^{2a}$ represents a hydroxyl-protecting group and $R^3$ is as defined above, and then reducing the optically active compound of formula (3a) or (3b) to obtain, respectively, an optically active compound represented by formula (4a):

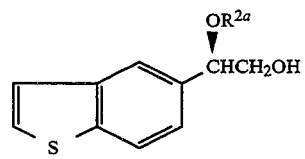

(4a)

or formula (4b):

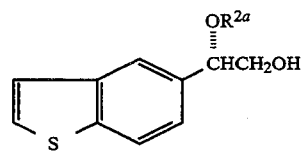

(4b)

wherein $R^{2a}$ is as defined above, and subsequently reacting the compound thus obtained with a compound represented by formula (5) or its salt:

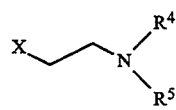

(5)

wherein $R^4$ and $R^5$ are as defined above and X represents a removable group, in the presence of a de-acidifying agent, and then, if desired, removing the hydroxyl-protecting group.

This invention further provides a novel intermediate represented by formula (7):

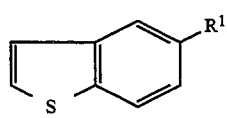

(7)

wherein $R^1$ is as defined above.

In the present specification, unless otherwise specified, the term "halogen atom" means a fluorine, chlorine, bromine or iodine atom; the term "lower alkyl group" means a $C_{1-6}$ alkyl group, for example, methyl, ethyl, n-propyl, isopropyl, n-butyl, isobutyl, tert-butyl, pentyl or hexyl; the term "lower alkylsulfonyloxy group" means a $C_{1-6}$ alkylsulfonyloxy group, and the term "arylsulfonyloxy group" means a phenylsulfonyloxy or naphthylsulfonyloxy group.

The hydroxyl-protecting group in the definition of $R^2$ and the carboxyl-protecting group in the definition of $R^3$ includes conventional hydroxyl-protecting groups and conventional carboxyl-protecting groups, respectively. Specific examples thereof include the protective groups mentioned in Protective Groups in Organic Synthesis by Theodora W. Greene published by John Wiley & Sons, Inc. (1981) and Japanese Patent Application Kokoku No. 60-52,755 and the like.

More specifically, the hydroxyl-protecting group includes, substituted methyl groups such as methoxymethyl, tert-butoxymethyl, 2-methoxyethoxymethyl, 2,2,2-trichloroethoxymethyl, tetrahydropyranyl, tetrahydrothiopyranyl, 4-methoxytetrahydropyranyl, tetrahydrofuranyl and the like; substituted ethyl groups such as 1-ethoxyethyl, 1-methyl-1-methoxyethyl, 2,2,2-trichloroethyl, tert-butyl, allyl, cinnamyl, p-chlorophenyl and the like; substituted benzyl groups such as p- methoxybenzyl, diphenylmethyl and the like; silyl groups such as trimethylsilyl, tert-butyldimethylsilyl, tert-butyldiphenylsilyl, methyl-di-tert-butylsilyl and the like; etc., and the carboxyl-protecting group includes C$_{1-6}$alkyl groups which may be substituted by halogen atoms such as methyl, ethyl, propyl, tert-butyl, 2-chloroethyl, 2,2,2-trichloroethyl and the like; aralkyl groups such as benzyl, diphenylmethyl, triphenylmethyl and the like; allyl group; cinnamyl group; silyl groups such as trimethylsilyl, tert-butyldimethylsilyl, phenyldimethylsilyl and the like; phenacyl group; lower alkylthio-lower alkyl groups such as methylthiomethyl, 2-methylthioethyl and the like; 4-piperonyl group; etc.

Next, an explanation is made of the present process and a process for producing the intermediate.

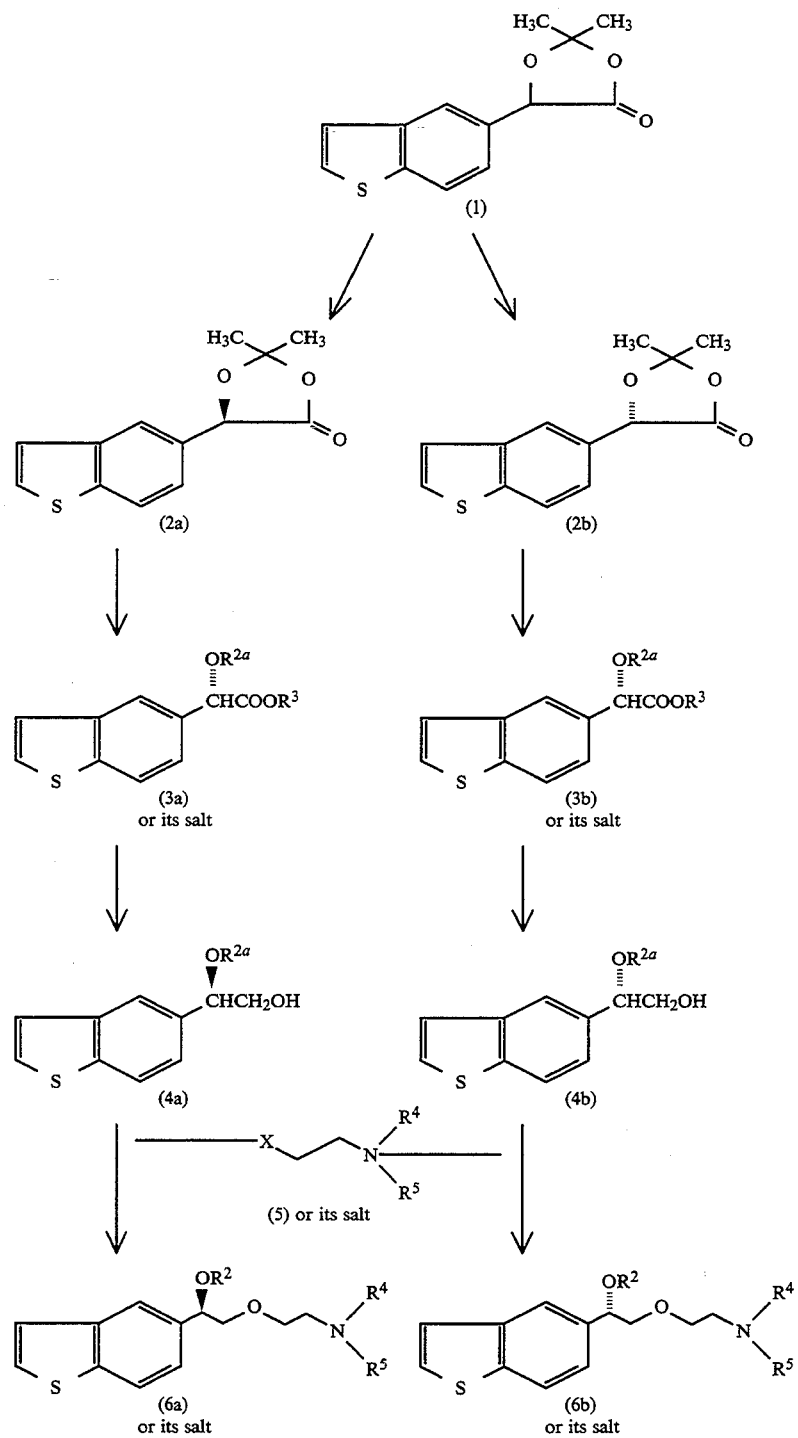

In the above formulas, $R^2$, $R^{2a}$, $R^3$, $R^4$, $R^5$ and X are as defined above.

The salts of the compounds of formulas (6a) and (6b) include salts with mineral acids such as hydrochloric acid, hydrobromic acid, sulfuric acid, phosphoric acid and the like; salts with carboxylic acids such as formic acid, acetic acid, oxalic acid, fumaric acid, maleic acid, malic acid, tartaric acid, aspartic acid and the like; salts with sulfonic acids such as methanesulfonic acid, benzenesulfonic acid, p-toluene-sulfonic acid, naphthalenesulfonic acid and the like; etc.

The salts of the compounds of formulas (3a) and (3b) in which $R^3$ is a hydrogen atom include salts with alkali metals such as lithium, sodium, potassium and the like; salts with alkaline earth metals such as barium, calcium and the like; salts with organic amines such as propylamine, butylamine, isobutylamine, octylamine, benzylamine, phenethylamine, diethylamine, diisopropylamine, triethylamine, methylpiperidine, methylpiperazine, aniline, leucinehydrazide and the like.

The salts of the compound of formula (5) include salts with mineral acids such as hydrochloric acid, hydrobromic acid, sulfuric acid, phosphoric acid and the like.

The removable group includes, for example, halogen atoms, lower alkylsulfonyloxy groups and arylsulfonyloxy groups.

The production process is explained in more detail below in the order of the steps shown in the above production route.

(1) Process for Producing Compound of Formula (2a) or (2b) (Racemization-Preferential Crystallization Method)

Into a supersaturated solution of a compound of formula (1) was inoculated configuration (+) or (−) crystals of the same compound as seed crystals in the presence of a racemization catalyst to preferentially crystallize the compound in the optically active form corresponding to the crystals inoculated.

The solvent to be used in said reaction includes solvents, the solubilities of the compound of formula (1) in which are suitable, for example, aliphatic hydrocarbons such as petroleum ether, petroleum benzine, ligroin, n-hexane, cyclohexane and the like; ethers such as diethyl ether, diisopropyl ether and the like; aromatic hydrocarbons such as benzene, toluene and the like; esters such as ethyl acetate and the like; secondary alcohols such as isopropanol, cyclohexanol and the like; tertiary alcohols such as tert-butanol, tert-amyl alcohol and the like; ketones such as acetone, methyl ethyl ketone, cyclopentanone and the like; halogenated hydrocarbons such as methylene chloride, chloroform and the like; nitriles such as acetonitrile and the like; amides such as N,N-dimethylformamide and the like; sulfoxides such as dimethylsulfoxide and the like; and mixtures thereof. In particular, tertiary alcohol and a mixture of a tertiary alcohol with one of the above-mentioned solvents are preferred.

Moreover, a solvent which may be added in order to control the solubility includes aliphatic hydrocarbons such as petroleum ether, hexane, cyclohexane and the like.

The racemization catalyst includes organic bases such as triethylamine, 1,8-diazabicyclo[5.4.0]-7-undecene (DBU), 1,5-diazabicyclo[4.3.0]non-5-ene (DBN), 1,4-diazabicyclo[2.2.2]octane, N-methylpiperazine and the like; and organic solvent-soluble quaternary ammonium salts such as tetrabutylammonium fluoride and the like; etc.

The amount of the racemization catalyst used may be 0.001-0.10 mole per mole of the compound of formula (1).

The amount of the seed crystals inoculated and the particle size of the crystals are not critical; however, it is preferable to use seed crystals in the form of crystals or in the form of a suspension in the same solvent in an amount of about 0.1–10% by weight based on the weight of the compound of formula (1).

The operation temperature is not critical, and the operation can be conducted at the boiling point of the solvent used. However, it is necessary to adjust the temperature so that a stable supersaturated solution of the compound of formula (1) can be obtained based on the solubility of the compound in the solvent.

(2) Process for Producing Compound of Formula (3a) or (3b)

(i) The compound of formula (3a) or (3b) can be prepared, respectively, by subjecting the compound of formula (2a) or (2b) to alcoholysis in the presence of an acid catalyst, and then introducing a hydroxyl-protecting group into the alcoholysis product in a manner known per se.

The alcohol to be used in the above alcoholysis includes, for example, $C_{1-6}$alkyl alcohols such as methanol, ethanol and the like; and aralkyl alcohols such as benzyl alcohol and the like; etc.

The acid catalyst used in the above reaction includes, for example, protonic acids such as hydrochloric acid, sulfuric acid, methanesulfonic acid, trifluoromethanesulfonic acid, p-toluenesulfonic acid, dichloroacetic acid and the like; and Lewis acids such as aluminum chloride, boron trifluoride, boron trichloride and the like.

The alcoholysis may be conducted in a solvent which does not adversely affect the reaction such as benzene, toluene, methylene chloride, diethyl ether, tetrahydrofuran and the like.

In the alcoholysis, the amount of the alcohol used is preferably 1 mole or more per mole of the compound of formula (2a) or (2b) and the amount of the acid catalyst used is preferably 0.1–30 moles per mole of the compound of formula (2a) or (2b).

It is sufficient that the above reaction is conducted at a temperature of 0°–120° C. for a period of 1–24 hours.

The hydroxyl-protecting group used in the subsequent introduction of a hydroxyl-protecting group is preferably a group which is stable against alkalis and can be removed under acidic or neutral conditions, and includes, for example, conventional substituted methyl groups such as methoxymethyl, 2-methoxyethoxymethyl, 2,2,2-trichloroethoxymethyl, tetrahydropyranyl, tetrahydrofuranyl and the like; conventional substituted ethyl groups such as 1-ethoxyethyl, tert-butyl and the like; conventional substituted benzyl groups such as p-methoxybenzyl, diphenylmethyl and the like; conventional silyl groups such as tert-butyldimethysilyl group, tert-butyldiphenylsilyl and the like; etc.

(ii) Furthermore, the free carboxylic acid of formula (3a) or (3b) can be obtained, respectively, by subjecting the compound of formula (2a) or (2b) to hydrolysis.

(3) Process for Producing Compound of Formula (4a) or (4b)

The compound of formula (4a) or (4b) can be prepared, respectively, by subjecting the compound of formula (3a) or (3b) to conventional ester-reduction.

Specifically, the ester-reduction can be conducted according to, for example, the method described in Shin Jikken Kagaku Kouza, Vol. 15, (II) editted by Chemical Society of Japan, pages 29–216 (1977) published by Maruzen. The reducing agent which may be used therein is preferably lithium borohydride or sodium borohydride, and the ester-reduction can be conducted in the presence or absence of a metal salt such as lithium chloride, lithium bromide, calcium chloride, cobalt chloride, nickel chloride or the like.

This reaction is usually conducted in the presence of a solvent, and the solvent includes alcohols such as methanol, ethanol, isopropanol and the like; ethers such as diethyl ether, tetrahydrofuran, diethylene glycol dimethyl ether and the like; nitriles such as acetonitrile and the like; amides such as N,N-dimethylacetamide and the like. These solvents may be used alone or in admixture of two or more.

In the above reaction, the amount of the reducing agent used is preferably 0.75-5 moles per mole of the compound of formula (3a) or (3b), and the reaction may be conducted at a temperature of 0°-60° C. for a period of 1-48 hours.

(4) Process for Producing Compound of Formula (6a) or (6b)

The compound of formula (6a) or (6b) or its salt can be prepared, respectively, by reacting the compound of formula (4a) or (4b) with a compound of formula (5) or its salt in the presence of a de-acidifying agent, and then, if desired, removing the hydroxyl-protecting group.

Specifically, the compound of formula (6a) or (6b) can be prepared according to, for example, the method described in Tetrahedron Letters, Vol. 38, pages 3251-3254 (1975) and Shin Jikken Kagaku Kouza, Vol. 14, (I) edited by Chemical Society of Japan, pages 567-611 (1977) published by Maruzen. The de-acidifying agent includes, for example, sodium hydride, sodium hydroxide, potassium hydroxide, potassium tert-butoxide and the like. The solvent which may be used in the above reaction includes aromatic hydrocarbons such as benzene, toluene, xylene and the like; ethers such as tetrahydrofuran, dioxane, diethylene glycol dimethyl ether and the like; amides such as dimethylformamide, N-methylpyrrolidone and the like; halogenated hydrocarbons such as methylene chloride, dichloroethane and the like; sulfoxides such as dimethylsulfoxide and the like; etc. These solvents may be used alone or in admixture of two or more.

The above reaction can be conducted in the presence or absence of a catalyst and in the presence or absence of water. The catalyst which may be used is a conventional quaternary ammonium salt phase transfer catalyst, and preferred are tetra-n-butylammonium hydrogensulfate, tetra-n-butylammonium iodide and the like.

In the above reaction, the amount of the compound of formula (5) used may be 1 mole or more per mole of the compound of formula (4a) or (4b), and the amount of the catalyst may be 0.01-0.15 mole per mole of the compound of formula (4a) or (4b).

The above reaction may be conducted at a temperature of 0°-150° C. for a period of 1-24 hours.

After the reaction, if desired, the hydroxyl-protecting group may be removed in a manner known per se.

Next, an explanation is made of the process for producing a compound of formula (1).

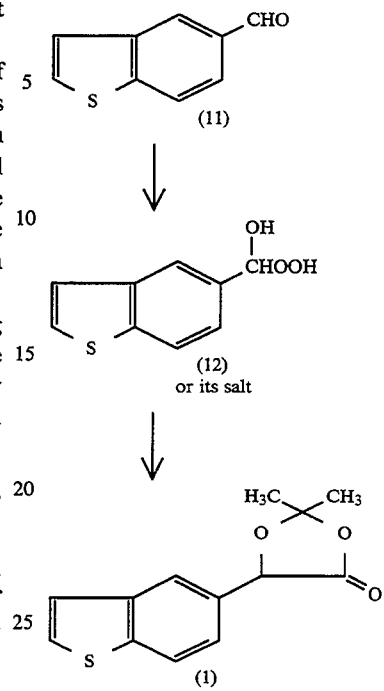

The salt of the compound of formula (12) includes the salts mentioned as to the compounds of formulas (3a) and (3b) in which $R^3$ is a hydrogen atom.

(I) Process for producing Compound of Formula (12) or Its Salt

The compound of formula (12) and its salt can be prepared according to, for example, the method described in J. Org. Chem., Vol. 33, pages 2565-2566 (1968). Specifically, (±)-2-(benzo[b]thiophen-5-yl)-2-hydroxyacetic acid [the compound of formula (12)] or its salt can be prepared by condensing a compound of formula (11) with bromoform in the presence of a base such as lithium hydroxide and then subjecting the condensation product to hydrolysis.

(II) Method of Production of Optically Active Form of Compound of Formula (12) or Its Salt by Optical Resolution Method using Optical Resolution Agent The methods described in Japanese Patent Application Kokai (Laid-Open) Nos. 54-24,849 and 55-147,236 and the like can be used. Specifically, an optically active compound or its salt can be prepared by subjecting the compound of formula (12) or its salt to optical resolution with an optically active amine, for example, optically active 2-aminobutanol or α-phenethylamine to obtain a desired diasteric salt and then de-salting the diasteric salt with an acid.

(III) Process for Producing Compound of Formula (1)

The method described in, for example, Bull. Soc. Chim. Fr., pages 332-340 (1970) can be used. Specifically, the compound of formula (1) can be prepared by reacting the compound of formula (12) or its salt with acetone, isopropenyl acetate or 2,2-dimethoxypropane in the presence or absence of an acid catalyst.

This invention is explained in more detail below referring to Examples. However, the Examples are merely illustrative and not by way of limitation.

In the Examples, the term "% e.e." for optical purity is the percentage of enantiomeric excess.

EXAMPLE 1

A mixture of 100 g of benzo[b]thiophen-5-yl-carbardehyde, 195 g of bromoform and 400 ml of dioxane was dropwise added to a suspension of 129 g of lithium hydroxide monohydrate in 400 ml of water with stirring at 50° C. over 4 hours. The reaction mixture was stirred at the same temperature for 2 hours, and thereafter, cooled to 20° C. The crystals separated were collected by filtration and suspended in a mixture of 768 ml of toluene and 256 ml of water. To the suspension was added 110 ml of 6N hydrochloric acid with stirring. The resulting mixture was stirred under reflux for 1 hour, and then cooled to 20° C. The crystals separated were collected by filtration to obtain 107 g (yield: 84%) of colorless crystals of (±)-2-(benzo[b]thiophen-5-yl)-2-hydroxyacetic acid. The crystals were recrystallized from isopropanol to obtain colorless crystals having a melting point of 151°–152° C.

IR (KBr) cm$^{-1}$: 3242, 1730, 1691.

EXAMPLE 2

(1) In 95 ml of acetone was suspended 15.78 g of (±)-2-(benzo[b]thiophen-5-yl)-2-hydroxyacetic acid, and 7.11 ml of R-(−)-2-aminobutanol was added thereto, after which the resulting mixture was dissolved by heating. The solution was gradually cooled with stirring and the crystals separated were collected by filtration to obtain 16.71 g (yield: 74.2%) of crude crystals of (−)-2-(benzo[b]thiophen-5-yl)-2-hydroxyacetic acid.R-(−)-2-aminobutanol salt. This was subjected to repeated recrystallization from isopropanol to obtain 5.58 g (yield: 24.8%) of colorless crystals having a melting point of 156°–157° C.

$[\alpha]_D$ −78.3° (24° C., C=1.0, H$_2$O).

IR (KBr)cm$^{-1}$: 3386, 2970, 1636, 1601.

(2) To 5.58 g of (−)-2-(benzo[b]thiophen-5-yl)-2-hydroxyacetic acid.R-(−)-2-aminobutanol salt were added 56 ml of water and 56 ml of ethyl acetate, and the pH was adjusted to 1.0 with 6N hydrochloric acid, after which the organic layer was separated. The organic layer separated was washed successively with water and an aqueous saturated sodium chloride solution, and then dried over anhydrous magnesium sulfate. The solvent was removed under reduced pressure, and diisopropyl ether was added to the residue thus obtained. The crystals thus separated were collected by filtration to obtain 3.78 g (yield: 96.8%) of crude crystals of (−)-2-(benzo[b]thiophen-5-yl)-2-hydroxyacetic acid. The crystals were recrystallized from acetone/benzene (volume ratio: ½) to obtain colorless crystals having a melting point of 167°–168° C.

$[\alpha]_D$ −142.3° (24° C., C=1.0, CH$_3$OH).

IR (KBr) cm$^{-1}$: 3315, 1685.

EXAMPLE 3

In 500 ml of acetone was suspended 100 g of (±)-2-(benzo[b]thiophen-5-yl)-2-hydroxyacetic acid, and 5.12 ml of conc. sulfuric acid was dropwise added thereto at −10° C. The suspension was stirred for a further one hour at the same temperature, and thereafter, 60 ml of 3.2N aqueous ammonia was dropwise added thereto at the same temperature. The crystals separated were collected by filtration to obtain 10.25 g (yield: 86%) of colorless crystals of (±)-2,2-dimethyl-5-(benzo[b]thiophen-5-yl)-1,3-dioxolan-4-one. The crystals were recrystallized from isopropanol to obtain colorless crystals having a melting point of 87°–88° C.

IR (KBr) cm$^{-1}$: 1790.

EXAMPLE 4

In 300 ml of tert-amyl alcohol was dissolved by heating 100 g of (±)-2,2-dimethyl-5-(benzo[b]thiophen-5-yl)-1,3-dioxolan-4-one. To the resulting solution was added 4.6 g of 1,8-diazabicyclo[5.4.0]-7-undecene at 50° C., and thereinto was then inoculated a suspension of 0.5 g of (−)-2,2-dimethyl-5-(benzo[b]thiophen-5-yl)-1,3-dioxolan-4-one in 1.5 ml of tert-amyl alcohol. The mixture thus obtained was stirred at 50° C. for 1 hour, and then gradually cooled to 25° C. over 4 hours, after which the mixture was stirred for a further 30 minutes at the same temperature. The crystals thus separated were collected by filtration, washed successively with 150 ml of tert-amyl alcohol and 135 ml of isopropanol and then dried to obtain 88 g of colorless crystals.

$[\alpha]_D$ −71.0° (24° C., C=1.0, CHCl$_3$).

Optical purity: 96.2% e.e..

Recrystallization thereof from isopropanol gave 81 g (yield: 81%) of (−)-2,2-dimethyl-5-(benzo[b]thiophen-5-yl)-1,3-dioxolan-4-one with an optical purity of 99% e.e. or more.

Melting point: 116°–117° C.

$[\alpha]_D$ −73.8° (24° C., C=1.0, CHCl$_3$).

IR (KBr) cm$^{-1}$: 1790.

EXAMPLE 5

Using (+)-2,2-dimethyl-5-(benzo[b]thiophen-5-yl)-1,3-dioxolan-4-one as seed crystals, 6 g of (±)-2,2-dimethyl-5-(benzo[b]thiophen-5-yl)-1,3-dioxolan-4-one was treated in the same manner as in Example 4 to obtain 5.37 g of crude crystals having a melting point of 114°–116° C.

$[\alpha]_D$ 72.0° (24° C. C=1.0, CHCl$_3$).

Optical purity: 97.5% e.e..

Recrystallization thereof from isopropanol gave 5.10 g (yield: 85%) of colorless crystals of (+)-2,2-dimethyl-5-(benzo[b]thiophen-5-yl)-1,3-dioxolan-4-one with an optical purity of 99% e.e. or more.

Melting point: 116°–117° C.

$[\alpha]_D$ +73.8° (24° C., C=1.0, CHCl$_3$).

IR (KBr) cm$^{-1}$: 1790.

EXAMPLE 6

To a suspension of 10 g of (−)-2,2-dimethyl-5-(benzo[b]thiophen-5-yl)-1,3-dioxolan-4-one in 20 ml of methanol was dropwise added 1.07 ml of conc. sulfuric acid with water-cooling. The mixture thus obtained was stirred at 25° C. for 1.5 hours, and 50 ml of methylene chloride and 40 ml of water were added thereto, after which the resulting mixture was neutralized with sodium hydrogencarbonate. The organic layer thus formed was separated, washed with water and then dried over anhydrous magnesium sulfate. The solvent was removed by distillation under reduced pressure, and n-hexane was added to the residue thus obtained, after which the crystals separated were collected by filtration to obtain 8.77 g (yield: 98%) of colorless crystals of methyl (−)-2-(benzo[b]thiophen-5-yl)-2-hydroxyacetate having a melting point of 83°–84° C.

$[\alpha]_D$ −136° (24° C., C=1.0, CH$_3$OH).

IR (KBr) cm$^{-1}$: 3440, 1726.

In the same manner, methyl (+)-2-(benzo[b]thiophen-5-yl)-2-hydroxyacetate was obtained.

$[\alpha]_D$ +136° (24° C., C=1.0, CH$_3$OH).

EXAMPLE 7

(1) To a solution of 10 g of methyl (−)-2-(benzo[b]thiophen-5-yl)-2-hydroxyacetate in 50 ml of methylene chloride were added 4.92 g of 3,4-dihydro-2H-pyran and 1.13 g of pyridinium p-toluenesulfonate, and they were stirred at 28° C. for 3 hours. The reaction mixture was washed successively with water, an aqueous saturated sodium hydrogencarbonate solution and water, and thereafter, dried over anhydrous magnesium sulfate. The solvent was removed by distillation under reduced pressure to obtain colorless, oily methyl (−)-2-(benzo[b]thiophen-5-yl)-2-(tetrahydropyranyloxy)acetate.

(2) In 41.3 ml of ethanol was dissolved the methyl (−)-2-(benzo[b]thiophen-5-yl)-2-(tetrahydropyranyloxy)acetate, and to this solution was added 2.90 g of sodium borohydride, and the resulting mixture was stirred at 25° C. for 8 hours. Subsequently, 13.23 ml of acetone was 1 dropwise added with ice-cooling to decompose the excessive sodium borohydride, and thereafter, 138 ml of methylene chloride and 138 ml of water were added thereto, and the pH was adjusted to 8.5 with 2N hydrochloric acid. The organic layer formed was separated, washed with water, and then dried over anhydrous magnesium sulfate. The solvent was removed under reduced pressure, and the residue thus obtained was washed with petroleum ether to obtain 12.0 g (yield: 96%) of colorless (−)-2-(benzo[b]thiophen-5-yl)-2-(tetrahydropyranyloxy)ethanol as a diastereomer mixture.

Melting point: 62°–77° C.

IR (KBr) cm$^{-1}$: 3287, 2937, 2862, 1128, 1079, 1028, 986.

In the same manner, the following compounds were obtained:

(+)-2-(benzo[b]thiophen-5-yl)-2-(tetrahydropyranyloxy)ethanol;

(±)-2-(benzo[b]thiophen-5-yl)-2-(tetrahydropyranyloxy)ethanol.

EXAMPLE 8

In the same manner as in Example 3, 1 g of (−)-2-(benzo[b]thiophen-5-yl)-2-hydroxyacetic acid was treated to obtain 920 mg (yield: 77.2%) of colorless crystals of (−)-2,2-dimethyl-5-(benzo[b]thiophen-5-yl)-1,3-dioxolan-4-one having a melting point of 116°–117° C.

$[\alpha]_D$ −73.8° (24° C. C=1.0, CHCl$_3$).
IR (KBr) cm$^{-1}$: 1790.

EXAMPLE 9

From the racemic resolution filtrate in Example 2 (1), the solvent was removed, and thereafter, treated in the same manner as in Example 2 (2) to obtain 3.02 g (yield: 19.1%) of (+)form-rich 2-(benzo[b]thiophen-5-yl)-2-hydroxyacetic acid.

$[\alpha]_D$ +32.5° (24° C., C=1.0, CH$_3$OH).
Optical purity: 22.8% e.e..

Subsequently, this was treated in the same manner as in Example 3 to obtain 2.52 g (yield: 70%) of colorless crystals of (+)form-rich 2,2-dimethyl-5-(benzo[b]thiophen-5-yl)-1,3-dioxolan-4-one.

$[\alpha]_D$ +29.1° (24° C., C=1.0, CHCl$_3$).
Optical purity: 39.5% e.e..

This was subjected to repeated recrystallization from isopropanol to obtain colorless crystals of (+)-2,2-dimethyl-5-(benzo[b]thiophen-5-yl)-1,3-dioxolan-4-one having a melting point of 116°–117° C.

$[\alpha]_D$ +73.8° (24° C., C=1.0, CHCl$_3$).
IR (KBr) cm$^{-1}$: 1790.

EXAMPLE 10

To a solution of 6.90 g of (±)-2-(benzo[b]thiophen-5-yl)-2-hydroxyacetic acid in 50 ml of methanol was added 6 ml of conc. sulfuric acid. The solution was refluxed for 1 hour, and thereafter, 250 ml of ethyl acetate and 250 ml of water were added to the resulting mixture, and the mixture was neutralized with sodium hydrogencarbonate. The organic layer formed was separated, washed successively with water and an aqueous saturated sodium chloride solution and then dried over anhydrous magnesium sulfate. The solvent was removed by distillation under reduced pressure, and isopropanol was added to the residue thus obtained. The crystals thus separated were collected by filtration to obtain 6.25 g (yield: 85%) of colorless crystals of methyl (±)-2-benzo[b]thiophen-5-yl)-2-hydroxyacetate having a melting point of 84°–86° C.

IR (KBr) cm$^{-1}$: 3440, 1726.

In the same manner, the following compounds were obtained:

Methyl (+)-2-(benzo[b]thiophen-5-yl)-2-hydroxyacetate;

Methyl (−)-2-(benzo[b]thiophen-5-yl)-2-hydroxyacetate.

EXAMPLE 11

In a mixture of 8.5 ml of tetrahydrofuran and 3 ml of water was suspended 2.0 g of (−)-2,2-dimethyl-5-(benzo[b]thiophen-5-yl)-1,3-dioxolan-4-one, and to the suspension was dropwise added 0.60 g of sulfuric acid with ice-cooling, after which the resulting mixture was stirred at 20° C. for 24 hours. To the reaction mixture were added 20 ml of ethyl acetate and 20 ml of water, and the organic layer formed was separated. The organic layer obtained was dried over anhydrous magnesium sulfate, and the solvent was removed by distillation under reduced pressure to obtain 1.65 g (yield: 98.3%) of crystals of (−)-2-(benzo[b]thiophen-5-yl)-2-hydroxyacetic acid. The crystals were recrystallized from isopropanol to obtain colorless, needle crystals having a melting point of 167.6°–168.0° C.

$[\alpha]_D$ −142.3° (20° C., C=1.0, CH$_3$OH).
IR (KBr) cm$^{-1}$: 3315, 2641, 1684.

EXAMPLE 12

To a mixture of 10 ml of toluene and 100 ml of a 50% aqueous sodium hydroxide solution were added 10 g of (−)-2-(benzo[b]thiophen-5-yl)-2-(tetrahydropyranyloxy)ethanol, 8.04 g of 2-(N,N-diethylamino)ethyl chloride hydrochloride and 610 mg of tetra-n-butylammonium hydrogensulfate, and the resulting mixture was refluxed for 1.5 hours. The reaction mixture was cooled to 20° C., and thereto were then added 90 ml of toluene and 150 ml of water, after which the organic layer formed was separated. The aqueous layer was extracted with 30 ml of toluene, and the extract obtained was combined with the organic layer previously separated, and the mixture was washed with water. Thereafter, 60 ml of water was added to the organic layer, and the pH was adjusted to 0.5 with 6N hydrochloric acid, after which the mixture was stirred at 25° C. for 1 hour. The aqueous layer was separated and washed with ethyl acetate, and thereto was added 40 ml of ethyl acetate, after which the pH was adjusted to 10.2 with potassium carbonate. The organic layer formed was separated, washed successively with water and an aqueous saturated sodium chloride solution, and then dried over anhydrous magnesium sulfate. The solvent was removed by distillation under reduced pressure, and the residue thus obtained were dissolved in 60 ml of ethyl acetate and 40 ml of acetone to form a solution. To the solution was added 7 ml of a solution of hydrogen chloride in ethanol (6.1N). The solution was stirred at 20° C. for 2 hours, and the crystals thus separated were collected by filtration to obtain 10.7 g (yield: 90%) of (−)-1-(benzo[b]thiophen-5-yl)-2-[2-(N,N-diethylamino)ethoxy]ethanol hydrochloride. This was recrystallized from ethyl acetate-ethanol to obtain colorless needle crystals having a melting point of 120°–121° C.

$[\alpha]_D$ −26.3° (24° C. C=1.0, 0.1N hydrochloric acid).

IR (KBr) cm⁻: 3310, 2631, 1127, 1100.

In the same manner, the following compounds were obtained:

(+)-1-(Benzo[b]thiophen-5-yl)-2-[2-(N,N-diethylamino)ethoxy]ethanol hydrochloride;

(±)-1-(Benzo[b]thiophen-5-yl)-2-[2-(N,N-diethylamino)ethoxy]ethanol hydrochloride.

EXAMPLE 13

In 600 ml of tert-amyl alcohol was dissolved by heating 200 g of (±)-2,2-dimethyl-5-(benzo[b]thiophen-5-yl)-1,3-dioxolan-4-one. To the resulting solution was added 9.2 g of 1,8-diazabicyclo[5.4.0]-7-undecene at 54° C., and thereinto was then inoculated a suspension of 1.0 g of (−)-2,2-dimethyl-5-(benzo[b]thiophen-5-yl)-1,3-dioxolan-4-one in 3.0 ml of tert-amyl alcohol. The mixture thus obtained was stirred at the same temperature for 2 hours, and then gradually cooled to 25° C. over 4 hours, after which the mixture was stirred for a further 30 minutes at the same temperature. The crystals thus separated were collected by filtration, washed successively with 300 ml of tert-amyl alcohol and 270 ml of isopropanol and then dried to obtain 176 g of colorless crystals.

$[\alpha]_D$ −71.0° (24° C. C=1.0, CHCl₃).

Optical purity: 96.2% e.e..

Recrystallization thereof from isopropanol gave 162 g (yield: 81%) of (−)-2,2-dimethyl-5-(benzo[b]thiophen-5-yl)-1,3-dioxolan-4-one with an optical purity of 99% e.e. or more.

Melting point: 116°–117° C.

$[\alpha]_D$ −73.8° (24° C., C=1.0, CHCl₃).

IR (KBr) cm⁻¹: 1790.

What is claimed is:

1. A process for producing an optically active benzo[b]thiophen-5-yl derivative represented by formula (6a) or (6b) or a salt thereof:

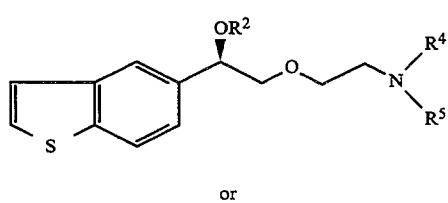

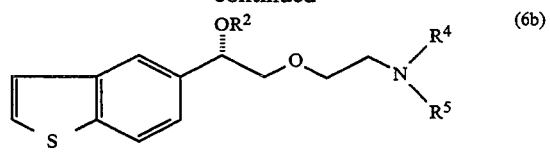

wherein $R^2$ represents a hydrogen atom or a hydroxyl-protecting group and $R^4$ and $R^5$, which may be the same or different, represent lower alkyl groups, which comprises inoculating into a supersaturated solution of a compound represented by formula (1):

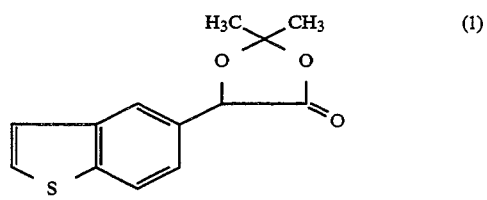

seed crystals of an optically active compound of formula (2a) when production of the compound of formula (6a) is intended or seed crystals of an optically active compound of formula (2b) when production of the compound of formula (6b) is intended, in the presence of a racemization catalyst to crystallize preferentially the corresponding optically active form of the compound of formula (1), to obtain, respectively, an optically active compound represented by formula (2a):

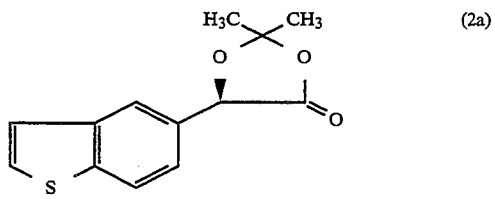

or formula (2b):

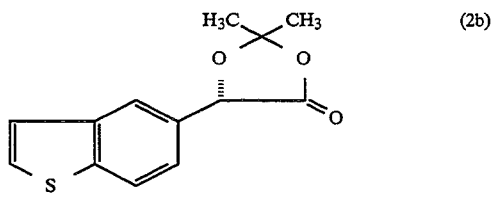

then subjecting the optically active compound obtained to alcoholysis or hydrolysis in the presence of an acid catalyst, subsequently introducing into the resulting product a hydroxyl-protecting group to obtain, respectively, an optically active compound represented by formula (3a):

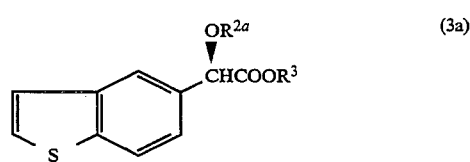

or formula (3b):

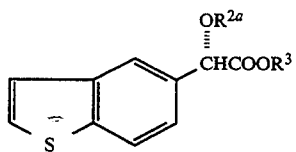

wherein $R^{2a}$ represents a hydroxyl-protecting group and $R^3$ represents a hydrogen atom or a carboxyl-protecting group, and then reducing the optically active compound of formula (3a) or (3b) to obtain, respectively, an optically active compound represented by formula (4a):

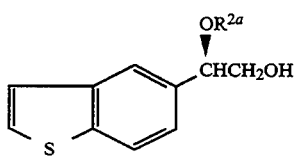

or formula (4b):

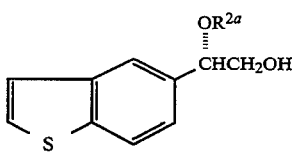

wherein $R^{2a}$ is as defined above, and subsequently reacting the compound thus obtained with a compound represented by formula (5) or its salt:

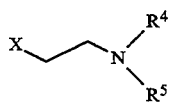

wherein $R^4$ and $R^5$ are as defined above and X represents a removable group, in the presence of a de-acidifying agent, and then, if desired, removing the hydroxyl-protecting group.

2. A process for producing an optically active benzo[b]thiophen-5-yl derivative represented by formula (6a) or (6b) or a salt thereof:

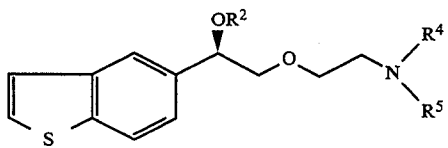

or

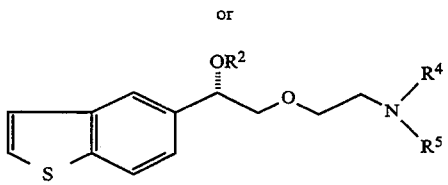

wherein $R^2$ represents a hydrogen atom or a hydroxyl-protecting group and $R^4$ and $R^5$, which may be the same or different, represent lower alkyl groups, which comprises reacting a compound represented by formula (4a) or (4b):

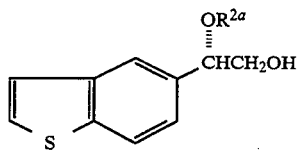

or

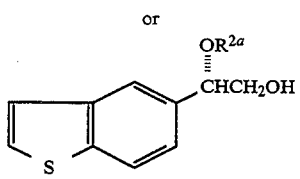

wherein $R^{2a}$ represents a hydroxyl-protecting group, with a compound represented by formula (5) or a salt thereof:

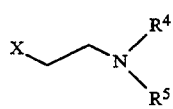

wherein $R^4$ and $R^5$ are as defined above and X represents a removable group, in the presence of a de-acidifying agent, and then, if desired, removing the hydroxyl-protecting group.

3. The process according to claim 1 or 2, wherein X is a halogen atom.

4. The process according to any one of claims 1 to 3, wherein the optically active benzo[b]thiophen-5-yl derivative is (−)-1-(benzo[b]thiophen-5-yl)-2-[2-(N,N-diethylamino)ethoxy]ethanol.

5. A compound represented by formula (7):

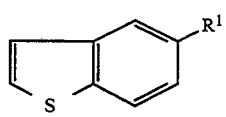

wherein $R^1$ represents a group represented by formula

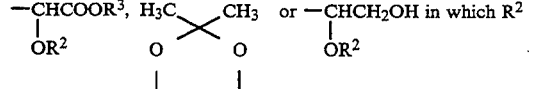
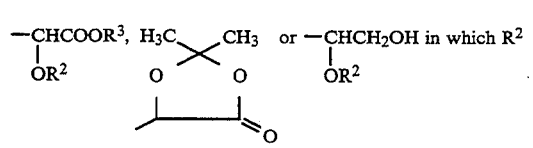

represents a hydrogen atom or a hydroxyl-protecting group and $R^3$ represents a hydrogen atom or a carboxyl-protecting group, an optically active form thereof or a salt thereof.

6. (−)-2,2-Dimethyl-5-(benzo[b]thiophen-5-yl)-1,3-dioxolan-4-one or (+)-2,2-dimethyl-5-(benzo[b]thiophen-5-yl)-1,3-dioxolan-4-one.